United States Patent [19]

Beck et al.

[11] 4,045,466
[45] Aug. 30, 1977

[54] 3-CYANOALKYLTHIO- OR 3-ALKOXYCARBONYLMETHYLTHIO-2,6-DI-NITROANILINES

[75] Inventors: James R. Beck, Indianapolis; Joseph A. Yahner, New Palestine, both of Ind.

[73] Assignee: Eli Lilly and Company, Indianapolis, Ind.

[21] Appl. No.: 719,309

[22] Filed: Aug. 31, 1976

Related U.S. Application Data

[63] Continuation-in-part of Ser. No. 668,360, March 19, 1976, abandoned, which is a continuation-in-part of Ser. No. 589,312, June 23, 1975, abandoned.

[51] Int. Cl.² ............... C07C 101/44; C07C 121/78
[52] U.S. Cl. .................. 260/465 E; 260/470; 424/304; 424/309
[58] Field of Search ............... 260/465 E, 470

[56] References Cited
U.S. PATENT DOCUMENTS 3,764,624  10/1973  Strong et al. ............... 260/574

Primary Examiner—Dolph H. Torrence
Attorney, Agent, or Firm—Dwight E. Morrison; Everet F. Smith

[57] ABSTRACT

A new class of 2,6-dinitroanilines bearing a cyanoalkylthio or alkoxycarbonylmethylthio group in the 3-position is disclosed. The new compounds possess activity against *Plasmopara viticola*, the causative organism of grape downy mildew.

5 Claims, No Drawings

3-CYANOALKYLTHIO- OR 3-ALKOXYCARBONYLMETHYLTHIO-2,6-DINITROANILINES

CROSS REFERENCE

This application is a continuation-in-part of copending application Ser. No. 668,360, filed Mar. 19, 1976, now abandoned which is a continuation-in-part of copending application Ser. No. 589,312, filed June 23, 1975, now abandoned.

BACKGROUND OF THE INVENTION

1. Field of the Invention

This invention relates to a new class of 2,6-dinitroanilines. More particularly, this invention relates to 2,6-dinitroanilines having a cyanoalkylthio or an alkoxycarbonylmethylthio group in the 3-position.

2. Description of the Prior Art

Beginning in the early 1960's, Soper disclosed that 2,6-dinitroanilines possess herbicidal activity, most notably preemergent herbicidal activity. See, for example, U.S. Pat. Nos. 3,111,403; 3,257,190; 3,332,769; and 3,367,949. Following Soper's lead, a large number of related dinitroanilines have also been shown to possess similar herbicidal activity. See, for example, U.S. Pat. Nos. 3,321,292; 3,617,251; 3,617,252; 3,672,864; 3,672,866; 3,764,624; and 3,877,924 and Belgian Patent 787,939.

Malichenko et al., *Fiziol. Aktiv. Veschestva* 1969, 2, 75–8; *C.A.* 73, 13451e (1970), disclose that some 2,6-dinitroanilines bearing a trifluoromethyl group in the 4-position possess some activity against *Phytophthora infestans*, the causative organism of late blight of tomatoes.

Clark et al., U.S. Pat. No. 3,119,736, disclose a broad class of compounds alleged to be fungicides. The generic description of such compounds includes dinitroanilines, but there is no specific disclosure of 2,6-dinitroanilines.

Zsolnai, *Biochemical Pharmacology* 5, 287–304 (1961), discloses that certain 2,4-dinitroanilines possess some fungicidal activity against various organisms. No 2,6-dinitroaniline was disclosed, nor was *Plasmopara viticola* among the organisms against which activity was shown.

Buczacki, *Ann. Appl. Biol.* 75, 25 (1973), tested five dinitroanilines against clubroot of cabbage with variable results. He concluded, however, that "dinitroanilines are unlikely to be of value in the control of clubroot."

Eshel and Katan, *Weed Science* 20, 243 (1972), observed the effects of four dinitroanilines against *Rhizoctonia solani* and *Fusarium oxysporum*. Three of the four test compounds decreased the growth of *R. solani* at the highest rates tested, but none of the four appreciably decreased the growth of *F. oxysporum* at any rate tested.

A study of trifluralin-treated soil by Breazeale and Camper, *Appl. Microbiol.* 19, 379 (1970), indicated that the actinomycete population increased as compared to the control, while the population of bacteria and fungi decreased.

SUMMARY OF THE INVENTION

This invention relates to a new class of 2,6-dinitroanilines having the following structure:

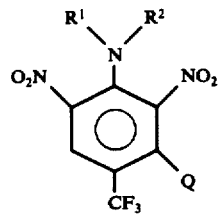

wherein
Q is $SCH_2CN$, $SCH_2CH_2CN$, or $SCH_2CO_2CH_3$;
$R^1$ is hydrogen or $C_1$-$C_3$ alkyl; and
when $R^1$ is hydrogen, $R^2$ is $C_1$-$C_6$ normal or branched alkyl containing no tertiary carbon atoms; and
when $R^1$ is $C_1$-$C_3$ alkyl, $R^2$ is $C_1$-$C_4$ nontertiary alkyl.

The novel compounds possess activity against *Plasmopara viticola*, the causative organism of grape downy mildew.

DESCRIPTION OF THE PREFERRED EMBODIMENT

In the above formula, all of the terms employed have the meanings normally ascribed to them in the chemical art. In order to illustrate the manner in which such terms are used, a few representative examples of compounds of the invention are named hereinafter.

2,6-Dinitro-N-(2-pentyl)-3-methoxycarbonylmethylthio-4-trifluoromethylaniline 2,6-Dinitro-N,N-diethyl-3-methoxycarbonylmethylthio-4-trifluoromethylaniline 2,6-Dinitro-N-propyl-3-methoxycarbonylmethylthio-4-trifluoromethylaniline 3-Cyanomethylthio-N,N-dipropyl-2,6-dinitro-4-trifluoromethylaniline 3-Cyanomethylthio-N-butyl-N-propyl-2,6-dinitro-4-trifluoromethylaniline 3-Cyanomethylthio-N-methyl-N-propyl-2,6-dinitro-4-trifluoromethylaniline 3-Cyanoethylthio-2,6-dinitro-N-methyl-N-ethyl-4-trifluoromethylaniline 3-Cyanomethylthio-2,6-dinitro-N,N-diethyl-2,6-dinitro-4-trifluoromethylaniline 3-Cyanoethylthio-2,6-dinitro-N-methyl-N-butyl-4-trifluoromethylaniline, and the like.

The novel compounds of this invention which bear a cyanomethylthio group in the 3-position are prepared from the corresponding 3-chloro compound by reaction with sodium sulfide and chloroacetonitrile. The 3-chloro compounds are intermediates in the preparation of the 1,3-phenylenediamines of U.S. Pat. No. 3,617,252, and the preparation of the 3-chloro compounds is described therein.

The preparation of a compound bearing a cyanomethylthio group in the 3-position is conveniently carried out using an inert solvent such as dimethylsulfoxide. Thus, a mixture of 3-chloro-N,N-diethyl-2,6-dinitro-4-trifluoromethylaniline and sodium sulfide nonahydrate in a suitable solvent such as dimethylsulfoxide is stirred for a period of time at about 0° C. There is then added chloroacetonitrile and the reaction mixture is stirred overnight at ambient room temperature. The reaction mixture is poured over ice and extracted with ether. The ether is evaporated and the residue recrystallized from a suitable solvent such as ethanol to yield in this case 3-cyanomethylthio-N,N-diethyl-2,6-dinitro-4-trifluoromethylaniline having a melting point of about 77°-79° C. The structure is confirmed by NMR spectrum.

The other sulfur-containing compounds are prepared by reaction of the 3-chloro compound with an appropriate mercapto compound in the presence of an alkali metal hydroxide such as lithium hydroxide or potassium hydroxide. Thus for example, 3-chloro-2,6-dinitro-N-methyl-4-trifluoromethylaniline and β-mercaptopropionitrile are dissolved in a suitable inert solvent such as dimethylformamide and cooled to about 0° C, and to the mixture there is added portionwise lithium hydroxide. The reaction mixture is then warmed to about 25° C. and stirred for a period of time sufficient to promote substantially complete reaction, such period of time being about 12 hours. The reaction mixture is worked up as described above and there is isolated, after recrystallization from ethanol, 3-cyanoethylthio-2,6-dinitro-N-methyl-4-trifluoromethylaniline having a melting point of about 116°-117° C.

Another of the sulfur compounds, namely 2,6-dinitro-N-(3-pentyl)-3-methoxycarbonylmethylthio-4-trifluoromethylaniline is prepared by adding an aqueous solution of potassium hydroxide to a mixture of 3-chloro-2,6-dinitro-N-(3-pentyl)-4-trifluoromethylaniline and methylthioglycolate in dimethylformamide. The mixture is allowed to warm to room temperature and is stirred for about an hour. The reaction mixture is worked up in the same manner as described previously to yield the desired product having a melting point of about 60°-61° C.

The preparation of the compounds is further illustrated by the following examples.

EXAMPLE 1

To a cold solution of 3.6 g. of 3-chloro-2,6-dinitro-N-(3-pentyl)-4-trifluoromethylaniline and 1.1 g. of methyl thioglycolate in 75 ml. of dimethylformamide was added dropwise 6.6 g. of potassium hydroxide in 5 ml. of water. The mixture was allowed to come to room temperature and stirred for one hour. The reaction mixture was poured over ice water and the product solidified. It was recovered by filtration and recrystallized from ethanol to yield 1.6 g. of 2,6-dinitro-N-(3-pentyl)-3-methoxycarbonylmethylthio-4-trifluoromethylaniline, m.p. 60°-61° C. The structure was confirmed by the NMR spectrum and elemental analysis.

Calculated: C, 42.35; H, 4.27; N, 9.88; Found: C, 42.43; H, 4.14; N, 9.89.

EXAMPLE 2

To 3.4 g. of 3-chloro-N,N-diethyl-2,6-dinitro-4-trifluoromethylaniline in 75 ml. of dimethylsulfoxide was added 2.4 g. of sodium sulfide nonahydrate in 10 ml. of water. The mixture was stirred at 25° C. for one hour, then 0.76 g. of chloroacetonitrile was added. The mixture was stirred at 25° C. for 12 hours and then poured over ice water. The product solidified, was extracted with ether, dried, the solvent evaporated and the residue recrystallized from ethanol to yield 2.7 g. of 3-cyanomethylthio-N,N-diethyl-2,6-dinitro-4-trifluoromethylaniline, m.p. 77°-79° C. The structure was confirmed by the NMR spectrum and elemental analysis.

Calculated: C, 41.27; H, 3.46; N, 14.81; Found: C, 41.15; H, 3.25; N, 14.65.

EXAMPLE 3

To a cold solution of 6.0 g. of 3-chloro-2,6-dinitro-N-methyl-4-trifluoromethylaniline and 4.0 ml. of β-mercaptopropionitrile in 100 ml. of dimethylformamide was added portionwise, with stirring, 0.6 g of lithium hydroxide. The solution was warmed to 25° C. and stirred for 12 hours. The reaction mixture was poured over ice water and the product solidified. It was recovered by filtration and recrystallized from ethanol to yield 5.8 g. of 3-cyanoethylthio-2,6-dinitro-N-methyl-4-trifluoromethylaniline, m.p. 116°-117° C. The structure was confirmed by the NMR spectrum and elemental analysis.

Calculated: C, 37.72; H, 2.59; N, 16.00; Found: C, 37.96; H, 2.84; N, 16.29.

EXAMPLE 4

To a cold solution of 21.3 g. of 3-chloro-2,6-dinitro-N-(3-pentyl)-4-trifluoromethylaniline and 10 ml. of β-mercaptopropionitrile in 200 ml. of dimethylformamide was added portionwise 2.0 g. of lithium hydroxide. The mixture was warmed to 25° C. and stirred for 2 hours. The reaction mixture was poured over ice water and the product oiled out. The solution was extracted with ether, washed with water, dried and concentrated to leave an oil. The product was chromatographed on a silica gel column with benzene and the solvent removed to yield 2.0 g. of 3-cyanoethylthio-2,6-dinitro-N-(3-pentyl)-4-trifluoromethylaniline. The structure was confirmed by the NMR spectrum and elemental analysis.

Calculated: C, 44.33; H, 4.22; N, 13.79; Found: C, 44.29; H, 4.22; N, 13.63.

The compounds of this invention exhibit utility in the control of grape downy mildew. Thus, the compounds have exhibited quite good activity against *Plasmopara viticola*, the causative organism of downy mildew of grape.

Tests against fungal foliar phytopathogens have demonstrated the powerful plant protective effect of the compounds of this invention. The first series of tests to be described exemplify the use of the compounds to reduce both the incidence and severity of grape downy mildew. In the tests described below, the compounds were applied as a solution or emulsion prepared by mixing 70 mg. of test compound with 1.925 ml of a mixture prepared from 500 ml. of acetone, 500 ml. of ethanol and 100 ml. of polyoxyethylene sorbitan monolaurate. The composition containing the test compound was then diluted with deionized water to obtain the desired concentration, measured in parts per million by weight (ppm.).

In the tests, the host plant was *Vitis vinifera*. The pathogen employed was *Plasmopara viticola*. Stock grape plants were grown in a greenhouse to serve as a supply of leaves for test use. On the test day, young expanding leaves were detached from the vines. One leaf was placed bottom side up in a plastic petri plate (100 × 20 mm.) and a water-soaked wad of cotton was wrapped around the petiole base. The petri plate contained a Whatman filter paper placed on top of an expanded plastic mat. The mat and filter paper kept the leaf above water flooding the bottom of the petri plate. Each test chemical was sprayed on the under side of the leaf and allowed to dry. All the test leaves were then inoculated by atomizing a conidial suspension over the under leaf surface and then each plate was covered. All the plates were placed on a shelf in a mist room at a temperature of 18°-20° C. and a light/dark cycle of 8/16 hours. Illumination was obtained from cool white fluorescent lamps ranging between 850–1000 foot-candles. Seven days after treatment, the leaves were examined and symptoms of disease were observed and results recorded using a scale of 1 to 5, wherein 1 indicates severe disease or no control and 5 indicates no disease or complete control.

The conidia employed as the inoculum for the test were obtained from recently infected leaf tissue stored in a chillroom at 5° C. The conidia were washed off the leaf surface with a brush and suspended in deionized water. The suspension was sprayed on leaf surfaces with a DeVilbiss atomizer.

In each test, two non-treated control leaves were sprayed with water containing the solvent-surfactant system. In addition, one leaf was sprayed with the commercial fungicide, manganese ethylene-1,2-bisdithiocarbamate (maneb).

The results obtained with a number of compounds of this invention are summarized in the following table. A wide range of concentrations of the test compounds was employed. A blank space in the table indicates that the compound was not tested at the indicated concentration. An asterisk indicates that the compound was phytotoxic at the indicated concentration. When a compound was tested more than once at the same concentration, the result given is an average.

dispersed in water with or without the aid of dispersing agents to form liquid sprayable mixtures.

The dinitroaniline compounds or a liquid or dust concentrate composition containing the active compound can be incorporated in intimate mixture with surface-active dispersing agents, such as nonionic emulsifying agents, to form spray compositions. Such compositions may be employed as such or may be dispersed in liquid carriers to form diluted sprays containing the active compound in any desired amount.

Similarly, the active dinitroaniline compounds can be compounded with a suitable water immiscible organic liquid and a surface-active dispersing agent to produce emulsifiable concentrates which can be further diluted with water and/or oil to form spray mixtures in the form of oil-water emulsions. Preferred dispersing agents to be employed in these compositions are oil soluble and include the nonionic emulsifiers, such as condensation products of alkylene oxides with phenols, sorbitan esters, complex ether alcohols and the like. Suitable organic liquids which can be employed include petroleum oils and distillates, toluene and synthetic organic oils. The surface-active dispersing agents are usually employed in liquid compositions in the amount from 0.1 to Table 1

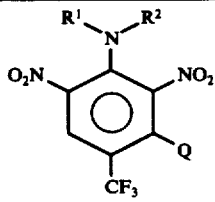

| Q | $R^1$ | $R^2$ | Downy Mildew Control (ppm.) | | | | |
|---|---|---|---|---|---|---|---|
|   |   |   | 800 | 400 | 200 | 100 | 50 |
| $SCH_2CO_2CH_3$ | H | $CH(C_2H_5)_2$ | 5 | 2 | * | 4+ | 1+ |
| $SCH_2CH_2CN$ | H | $CH_3$ | 1+ | 3 | 1 | | |
| $SCH_2CN$ | $C_2H_5$ | $C_2H_5$ | 2 | 3+ | 4 | 3+ | |
| $SCH_2CH_2CN$ | H | $CH(C_2H_5)_2$ | 4 | 4 | 4− | 1 | |

In accordance with standard agricultural practices, the novel compounds are preferably employed in liquid, powder or dust compositions containing one or more of the active compounds. In preparing such compositions, the 2,6-dinitroaniline compounds can be modified with one or more of a plurality of additaments including organic solvents, petroleum distillates, water or other liquid carriers, surface-active dispersing agents and finely divided inert solids. In such compositions, the dinitroaniline compound can be present in a concentration of from about 2 to about 98 percent by weight.

In the preparation of dust compositions, the dinitroanilines can be compounded with any of the finely divided solids such as pyrophyllite, talc, chalk, gypsum and the like. In such operations, the finely divided carrier is ground or mixed with the dinitroaniline or is wet with a solution of the dinitroaniline in a volatile organic solvent. Similarly, dust compositions containing the active compound can be prepared with various solid surface-active dispersing agents, such as fuller's earth, bentonite, attapulgite and other clays. Depending upon the proportions of ingredients, these dust compositions can be employed as concentrates and subsequently diluted with an additional solid surface-active dispersing agent or with pyrophyllite, chalk, talc, gypsum and the like to obtain the desired amount of active ingredient in a composition adapted to be employed for the control of phytopathogens. Also, such dust compositions can be 20% by weight of the composition.

The formulation of agricultural chemicals is a well-developed art and those skilled in the art will have no difficulty in preparing formulations of active dinitroaniline compounds for use in the practice of the method of this invention.

The exact concentration of the dinitroaniline compound for use in the control of phytopathogens can vary widely provided that an effective amount is applied to the host plant. The amount which is effective is dependent upon the particular compound employed and the severity of the infection. In general, good results are obtained using liquid compositions containing from about 2,000 to about 10 ppm. of the active compound. When dusts are used, good results are usually obtained with compositions containing from about 0.05 to 5.0% or more by weight of the active compound. Preferably, the compounds are applied at a rate of about 10 g. to about 2 kg. per hectare.

We claim:
1. A compound of the formula

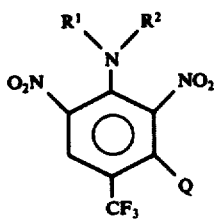

wherein

Q is SCH$_2$CN, SCH$_2$CH$_2$CN, or SCH$_2$CO$_2$CH$_3$;

R$^1$ is hydrogen or C$_1$-C$_3$ alkyl; and when R$^1$ is hydrogen, R$^2$ is C$_1$-C$_6$ normal or branched alkyl containing no tertiary carbon atom; and when R$^1$ is C$_1$-C$_3$ alkyl, R$^2$ is C$_1$-C$_4$ nontertiary alkyl.

2. A compound as in claim 1, said compound being 2,6-dinitro-N-(3-pentyl)-3-methoxycarbonylmethylthio-4-trifluoromethylaniline.

3. A compound as in claim 1, said compound being 3-cyanomethylthio-N,N-diethyl-2,6-dinitro-4-trifluoromethylaniline.

4. A compound as in claim 1, said compound being 3-cyanoethylthio-2,6-dinitro-N-methyl-4trifluoromethylaniline.

5. A compound as in claim 1, said compound being 3-cyanoethylthio-2,6-dinitro-N-(3-pentyl)-4-trifluoromethylaniline.